US 6,696,291 B2

(12) United States Patent
Shiver et al.

(10) Patent No.: US 6,696,291 B2
(45) Date of Patent: Feb. 24, 2004

(54) **SYNTHETIC HIV *GAG* GENES**

(75) Inventors: John W. Shiver, Doylestown, PA (US); Daniel C. Freed, Limerick, PA (US); Mary Ellen Davies, Norristown, PA (US); Margaret A. Liu, Rosemont, PA (US); Helen C. Perry, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/974,702

(22) Filed: Oct. 9, 2001

(65) Prior Publication Data

US 2003/0050468 A1 Mar. 13, 2003

Related U.S. Application Data

(63) Continuation of application No. 09/340,871, filed on Jun. 28, 1999, now abandoned, which is a continuation-in-part of application No. 09/017,981, filed on Feb. 3, 1998, now abandoned.
(60) Provisional application No. 60/037,854, filed on Feb. 7, 1997.

(51) Int. Cl.[7] .............................. C12N 5/06; C12N 5/00; C12Q 1/70; C12Q 1/68; C07H 21/04
(52) U.S. Cl. ............................ 435/339.1; 435/5; 435/6; 435/325; 536/23.1
(58) Field of Search .............................. 536/23.1; 435/5, 435/6, 325, 339.1

(56) References Cited

FOREIGN PATENT DOCUMENTS

| EP | 345242 A2 | 12/1989 |
|---|---|---|
| EP | 565794 A1 | 10/1993 |
| JP | 950007288 | 1/1995 |
| WO | WO 91/09869 | 7/1991 |
| WO | WO 94/16737 | 8/1994 |
| WO | WO 95/20660 | 8/1995 |
| WO | WO 96/09378 | 3/1996 |
| WO | WO 96/21356 | 7/1996 |
| WO | WO 97/11086 | 3/1997 |
| WO | WO 97/31115 | 8/1997 |

OTHER PUBLICATIONS

Andre, Stefanie; et al., Increased Immune Response Elicited by DNA Vaccination with a Synthetic gp120 Sequence with Optimized Codon Usage, 1998, Journal of Virology, pp. 1497–1503.

Bagarazzi, M. L.; et al., Nucleic Acid–Based Vaccines as an Approach to Immunization Against Human Immunodeficiency Virus Type–1, 1998, Carr. Top. Microbiol. Immunol.; vol. 226; pp. 107–143.

Belshe, Robert B.; et al., Safty and Immunogenicity of a Fully Glycosylated Recombinant gp160 Human Immunodeficiency Virus Type 1 Vaccine in Subjects at Low Risk of Infection, 1993, Journal of Infectious Diseases; vol. 168; pp. 1387–1395.

Chou, Kuo–Chen and Zhang, Chun–Ting, Diagrammatization of Codon Usage in 339 Human Immunodeficiency Virus Proteins and Its Biological Implication, 1992, Aids Research and Human Retroviruses; vol. 8; No. 12; pp. 1967–1976.

(List continued on next page.)

Primary Examiner—Hankyel T. Park
(74) Attorney, Agent, or Firm—Joseph Fischer; Van Dyke & Associates, P.A.

(57) ABSTRACT

Synthetic DNA molecules encoding HIV gag and modifications of HIV gag are provided. The codons of the synthetic molecules are codons preferred by the projected host cell. The synthetic molecules may be used as a polynucleotide vaccine which provides effective immunoprophylaxis against HIV infection through stimulation of neutralizing antibody and cell-mediated immunity.

20 Claims, 5 Drawing Sheets

OTHER PUBLICATIONS

Coney, Leslie; et al., Facilitated DNA inoculation induces anti–HIV–1 immunity in vivo, 1994, Vaccine; vol. 12; No. 16; pp. 1545–1551.

Fahey, J. L. and Schooley, R., Status of immune–based therapies in HIV infection and AIDS, 1992, Clin. Exp. Immunol; vol. 88; pp. 1–5.

Fox, Jeffrey L., No winners against AIDS, 1994, Bio/Technology; vol. 12; p. 128.

Fuller, Deborah Heydenburg and Haynes, Joel R., A Qualitative Progression in HIV Type 1 Glycoprotein 120–Specific Cytotoxic Cellular and Humoral Immune Responses in Mice Receiving a DNA–Based Glycoprotein 120 Vaccine, 1994, Aids Researchand Human Retroviruses; vol. 10; No. 11; pp. 1433–1441.

Haas, Jurgen; et al., Codon usage limitation in the expression of HIV–1 envelope glycoprotein, 1996, Current Biology; vol. 6; No. 3; pp. 315–324.

Haynes, Barton F.; et al., Update on the Issues of HIV Vaccine Development, 1996, Ann Med.; vol. 28; pp. 39–41.

Holler, Tod P.; et al., HIV1 integraseexpressed in *Escherichia coli* from a synthetic gene, 1993, Gene; vol. 136; pp. 323–328.

Lathe, R., Synthetic Oligonucleotide Probes Deduced from Amino Acid Sequence Data—Theoretical and Practical Considerations, 1985, J. Mol. Biol.; vol. 183; pp. 1–12.

Letvin, Norman L.; et al., Potent, protective anti–HIV immune responses generated by bimodal HIV envelope DNA plus protein vaccination, 1997, Proc. Natl. Acad. Sci. USA; vol. 94; pp. 9378–9383.

Liu, Margaret A.; et al., Vaccination of Mice and Nonhuman Primates using HIV–Gene–Containing DNA, 1996, Antibiot. chemother. Basel. Karger; vol. 48; pp. 100–104.

Morikawa, Yuko; Barsov, Eugene; and Jones, Ian, Legitimate and Illegitimate Cleavage of Human Immunodeficiency Virus Glycoproteins by Furin, 1993, Journal of Virology; vol. 67; pp. 3601–3604.

Myers, Gerald; et al. (Edited by), Human Retroviruses and AIDS; A Comilation and Analysis of Nucleic Acid and Amino Acid Sequences, 1990, Published by Theretical Biology and Biophysics Group T–10; pp. 1–A–74 thru 1–A–77.

Okuda, Kenji; et al., Induction of Potent Humoral and Cell–Mediated Immune Responses Following Direct Injection of DNA Encoding the HIV Type 1 env and rev Gene Products, 1995, Aids Research and Human Retroviruses; vol. 11; No. 8; pp. 933–943.

Powell, Michael F.; and Newman, Mark J. (Edited by), Vaccine design: the subunit and adjuvant approach, 1995, Published by Plenum Press; pp. 21, 654.

Rinaldo, Charles; et al., High Levels of Anti–Human Immunodeficiency Virus Type 1 (HIV–1) Memory Cytotoxic T–Lymphocyte Activity and Low Viral Load Are Associated with Lack of Disease in HIV–1–Infected Long–Term Nonprogressors, 1995, Journal of Virology; vol. 69; No. 9; pp. 5838–5842.

Shiver, John; et al., Cytotoxic T Lymphocyte and Helper T Cell Responses foloowing HIV Polynucleotide Vaccination, 1995, Annals New York Academy of Sciences; vol. 772; pp. 198–208.

Wang, Ban; et al., DNA Inoculation Induces Neutralizing Immune Responses Against Human Immunodeficiency Virus Type 1 in Mice and Nonhuman Primates, 1993, DNA and Cell Biology; vol. 9; pp. 799–805.

Wang, Bin; et al., Gene inoculation generates immune responses against human immunodeficiency virus type 1, 1993, Proc. Natl. Acad. Sci. USA; vol. 90; pp. 4156–4160.

Wang, Bin; et al., Vectors and Novel Vaccines; DNA Inoculation Induces Protective in Vivo Immune Responses against Cellular Challange with HIV–1 Antigen–Expressing Cells, 1994, Aids Research and Human Retroviruses; vol. 10; Supplement 2; pp. S35–S41.

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 1532 base pairs
      (B) TYPE: nucleic acid
      (C) STRANDEDNESS: double
      (D) TOPOLOGY: both    (ii) MOLECULE TYPE: cDNA    (iii) HYPOTHETICAL: NO    (iv) ANTI-SENSE: NO    (xi) SEQUENCE DESCRIPTION: SEQ ID NO: 1:

```
AGATCTACCA TGGGTGCTAG GGCTTCTGTG CTGTCTGGTG GTGAGCTGGA CAAGTGGGAG      60

AAGATCAGGC TGAGGCCTGG TGGCAAGAAG AAGTACAAGC TAAAGCACAT TGTGTGGGCC     120

TCCAGGGAGC TGGAGAGGTT TGCTGTGAAC CCTGGCCTGC TGGAGACCTC TGAGGGGTGC     180

AGGCAGATCC TGGGCCAGCT CCAGCCCTCC CTGCAAACAG GCTCTGAGGA GCTGAGGTCC     240

CTGTACAACA CAGTGGCTAC CCTGTACTGT GTGCACCAGA AGATTGATGT GAAGGACACC     300

AAGGAGGCCC TGGAGAAGAT TGAGGAGGAG CAGAACAAGT CCAAGAAGAA GGCCCAGCAG     360

GCTGCTGCTG GCACAGGCAA CTCCAGCCAG GTGTCCCAGA ACTACCCCAT TGTGCAGAAC     420

CTCCAGGGCC AGATGGTGCA CCAGGCCATC TCCCCCCGGA CCCTGAATGC CTGGGTGAAG     480

GTGGTGGAGG AGAAGGCCTT CTCCCCTGAG GTGATCCCCA TGTTCTCTGC CCTGTCTGAG     540

GGTGCCACCC CCCAGGACCT GAACACCATG CTGAACACAG TGGGGGGCCA TCAGGCTGCC     600

ATGCAGATGC TGAAGGAGAC CATCAATGAG GAGGCTGCTG AGTGGGACAG GCTGCATCCT     660

GTGCACGCTG GCCCCATTGC CCCCGGCCAG ATGAGGGAGC CCAGGGGCTC TGACATTGCT     720

GGCACCACCT CCACCCTCCA GGAGCAGATT GGCTGGATGA CCAACAACCC CCCCATCCCT     780
```

```
GTGGGGGAAA TCTACAAGAG GTGGATCATC CTGGGCCTGA ACAAGATTGT GAGGATGTAC      840

TCCCCCACCT CCATCCTGGA CATCAGGCAG GGCCCCAAGG AGCCCTTCAG GGACTATGTG      900

GACAGGTTCT ACAAGACCCT GAGGGCTGAG CAGGCCTCCC AGGAGGTGAA GAACTGGATG      960

ACAGAGACCC TGCTGGTGCA GAATGCCAAC CCTGACTGCA AGACCATCCT GAAGGCCCTG     1020

GGCCCTGCTG CCACCCTGGA GGAGATGATG ACAGCCTGCC AGGGGGTGGG GGGCCCTGGT     1080

CACAAGGCCA GGGTGCTGGC TGAGGCCATG TCCCAGGTGA CCAACTCCGC CACCATCATG     1140

ATGCAGAGGG GCAACTTCAG GAACCAGAGG AAGACAGTGA AGTGCTTCAA CTGTGGCAAG     1200

GTGGGCCACA TTGCCAAGAA CTGTAGGGCC CCCAGGAAGA AGGGCTGCTG GAAGTGTGGC     1260

AAGGAGGGCC ACCAGATGAA GGACTGCAAT GAGAGGCAGG CCAACTTCCT GGGCAAAATC     1320

TGGCCCTCCC ACAAGGGCAG GCCTGGCAAC TTCCTCCAGT CCAGGCCTGA GCCCACAGCC     1380

CCTCCCGAGG AGTCCTTCAG GTTTGGGGAG GAGAAGACCA CCCCCAGCCA GAAGCAGGAG     1440

CCCATTGACA AGGAGCTGTA CCCCCTGGCC TCCCTGAGGT CCCTGTTTGG CAACGACCCC     1500

TCCTCCCAGT AAAATAAAGC CCGGGCAGAT CT                                   1532
```

SYNTHETIC HIV *GAG* GENES

CROSS-REFERENCE TO RELATED APPLICATIONS

This application is a continuation of U.S. application Ser. No. 09/340,871, filed Jun. 28, 1999 now abandoned, which is a continuation in part of U.S. application Ser. No. 09/017,981, filed Feb. 3, 1998, now abandoned which claims benefit of 60/037,854, Feb. 7, 1997. The benefit of priority under 35 USC §120 is claimed for all of the foregoing applications.

STATEMENT REGARDING FEDERALLY-SPONSORED R&D

Not applicable

REFERENCE TO MICROFICHE APPENDIX

Not applicable

1. Field of Invention

HIV Vaccines.

2. Background of the Invention

Human Immunodeficiency Virus-1 (HIV-1) is the etiological agent of acquired human immune deficiency syndrome (AIDS) and related disorders. HIV-1 is an RNA virus of the Retroviridae family and exhibits the 5'LTR-gag-pol-env-LTR3' organization of all retroviruses. In addition, HIV-1 comprises a handful of genes with regulatory or unknown functions, including the tat and rev genes. The env gene encodes the viral envelope glycoprotein that is translated as a 160-kilodalton (kDa) precursor (gp160) and then cleaved by a cellular protease to yield the external 120-kDa envelope glycoprotein (gp120) and the transmembrane 41-kDa envelope glycoprotein (gp41). Gp120 and gp41 remain associated and are displayed on the viral particles and the surface of HIV-infected cells. Gp120 binds to the CD4 receptor present on the surface of helper T-lymphocytes, macrophages and other target cells. After gp120 binds to CD4, gp41 mediates the fusion event responsible for virus entry.

Infection begins when gp120 on the viral particle binds to the CD4 receptor on the surface of T4 lymphocytes or other target cells. The bound virus merges with the target cell and reverse transcribes its RNA genome into the double-stranded DNA of the cell. The viral DNA is incorporated into the genetic material in the cell's nucleus, where the viral DNA directs the production of new viral RNA, viral proteins, and new virus particles. The new particles bud from the target cell membrane and infect other cells.

Destruction of T4 lymphocytes, which are critical to immune defense, is a major cause of the progressive immune dysfunction that is the hallmark of HIV infection. The loss of target cells seriously impairs the body's ability to fight most invaders, but it has a particularly severe impact on the defenses against viruses, fungi, parasites and certain bacteria, including mycobacteria.

HIV-1 kills the cells it infects by replicating, budding from them and damaging the cell membrane. HIV-1 may kill target cells indirectly by means of the viral gp120 that is displayed on an infected cell's surface. Since the CD4 receptor on T cells has a strong affinity for gp120, healthy cells expressing CD4 receptor can bind to gp120 and fuse with infected cells to form a syncytium.

HIV-1 can also elicit normal cellular immune defenses against infected cells. With or without the help of antibodies, cytotoxic defensive cells can destroy an infected cell that displays viral proteins on its surface. Finally, free gag and gp120 protein may circulate in the blood of individuals infected with HIV-1. The free gp120 protein may bind to the CD4 receptor of uninfected cells, making them appear to be infected and evoking an immune response.

Infection with HIV-1 is almost always fatal, and at present there are no cures for HIV-1 infection. Effective vaccines for prevention of HIV-1 infection are not yet available. Because of the danger of reversion or infection, live attenuated virus probably cannot be used as a vaccine. Most subunit vaccine approaches have not been successful at preventing HIV infection. Treatments for HIV-1 infection, while prolonging the lives of some infected persons, have serious side effects. There is thus a great need for effective treatments and vaccines to combat this lethal infection.

Vaccination is an effective form of disease prevention and has proven successful against several types of viral infection. Determining ways to present HIV-1 antigens to the human immune system in order to evoke protective humoral and cellular immunity, is a difficult task. To date, attempts to generate an effective HIV vaccine have not been successful. In AIDS patients, free virus is present in low levels only. Transmission of HIV-1 is enhanced by cell-to-cell interaction via fusion and syncytia formation. Hence, antibodies generated against free virus or viral subunits are generally ineffective in eliminating virus-infected cells.

Vaccines exploit the body's ability to "remember" an antigen. After first encounters with a given antigen the immune system generates cells that retain an immunological memory of the antigen for an individual's lifetime. Subsequent exposure to the antigen stimulates the immune response and results in elimination or inactivation of the pathogen.

The immune system deals with pathogens in two ways: by humoral and by cell-mediated responses. In the humoral response lymphocytes generate specific antibodies that bind to the antigen thus inactivating the pathogen. The cell-mediated response involves cytotoxic and helper T lymphocytes that specifically attack and destroy infected cells.

Vaccine development with HIV-1 virus presents problems because HIV-1 infects some of the same cells the vaccine needs to activate in the immune system (i.e., T4 lymphocytes). It would be advantageous to develop a vaccine which inactivates HIV before impairment of the immune system occurs. A particularly suitable type of HIV vaccine would generate an anti-HIV immune response which recognizes HIV variants and which works in HIV-positive individuals who are at the beginning of their infection.

A major challenge to the development of vaccines against viruses, particularly those with a high rate of mutation such as the human immunodeficiency virus, against which elicitation of neutralizing and protective immune responses is desirable, is the diversity of the viral envelope proteins among different viral isolates or strains. Because cytotoxic T-lymphocytes (CTLs) in both mice and humans are capable of recognizing epitopes derived from conserved internal viral proteins, and are thought to be important in the immune response against viruses, efforts have been directed towards the development of CTL vaccines capable of providing heterologous protection against different viral strains.

It is known that $CD8^+$ CTLs kill virally-infected cells when their T cell receptors recognize viral peptides associated with MHC class I molecules. The viral peptides are derived from endogenously synthesized viral proteins, regardless of the protein's location or function within the virus. Thus, by recognition of epitopes from conserved viral proteins, CTLs may provide cross-strain protection. Peptides capable of associating with MHC class I for CTL recognition originate from proteins that are present in or pass through the cytoplasm or endoplasmic reticulum. In general, exogenous proteins, which enter the endosomal processing pathway (as in the case of antigens presented by MHC class II molecules), are not effective at generating $CD8^+$ CTL responses.

Most efforts to generate CTL responses have used replicating vectors to produce the protein antigen within the cell or have focused upon the introduction of peptides into the cytosol. These approaches have limitations that may reduce their utility as vaccines. Retroviral vectors have restrictions on the size and structure of polypeptides that can be expressed as fusion proteins while maintaining the ability of the recombinant virus to replicate, and the effectiveness of vectors such as vaccinia for subsequent immunizations may be compromised by immune responses against the vectors themselves. Also, viral vectors and modified pathogens have inherent risks that may hinder their use in humans. Furthermore, the selection of peptide epitopes to be presented is dependent upon the structure of an individual's MHC antigens and, therefore, peptide vaccines may have limited effectiveness due to the diversity of MHC haplotypes in outbred populations.

Benvenisty, N., and Reshef, L. [*PNAS* 83, 9551–9555, (1986)] showed that $CaCl_2$-precipitated DNA introduced into mice intraperitoneally (i.p.), intravenously (i.v.) or intramuscularly (i.m.) could be expressed. The i.m. injection of DNA expression vectors without $CaCl_2$ treatment in mice resulted in the uptake of DNA by the muscle cells and expression of the protein encoded by the DNA. The plasmids were maintained episomally and did not replicate. Subsequently, persistent expression has been observed after i.m. injection in skeletal muscle of rats, fish and primates, and cardiac muscle of rats. The technique of using nucleic acids as therapeutic agents was reported in WO90/11092 (Oct. 4, 1990), in which naked polynucleotides were used to vaccinate vertebrates.

It is not necessary for the success of the method that immunization be intramuscular. The introduction of gold microprojectiles coated with DNA encoding human growth hormone (HGH) into the skin of mice resulted in production of anti-HGH antibodies in the mice. A jet injector has been used to transfect skin, muscle, fat, and mammary tissues of living animals. Various methods for introducing nucleic have been reviewed. Intravenous injection of a DNA:cationic liposome complex in mice was shown by Zhu et al., [Science 261:209–211 (Jul. 9, 1993) to result in systemic expression of a cloned transgene. Ulmer et al., [*Science* 259:1745–1749, (1993)] reported on the heterologous protection against influenza virus infection by intramuscular injection of DNA encoding influenza virus proteins.

The need for specific therapeutic and prophylactic agents capable of eliciting desired immune responses against pathogens and tumor antigens is met by the instant invention. Of particular importance in this therapeutic approach is the ability to induce T-cell immune responses which can prevent infections or disease caused even by virus strains which are heterologous to the strain from which the antigen gene was obtained. This is of particular concern when dealing with HIV as this virus has been recognized to mutate rapidly and many virulent isolates have been identified [see, for example, LaRosa et al., Science 249:932–935 (1990), identifying 245 separate HIV isolates]. In response to this recognized diversity, researchers have attempted to generate CTLs based on peptide immunization. Thus, Takahashi et al., [*Science* 255:333–336 (1992)] reported on the induction of broadly cross-reactive cytotoxic T cells recognizing an HIV envelope (gp160) determinant. However, those workers recognized the difficulty in achieving a truly cross-reactive CTL response and suggested that there is a dichotomy between the priming or restimulation of T cells, which is very stringent, and the elicitation of effector function, including cytotoxicity, from already stimulated CTLs.

Wang et al. reported on elicitation of immune responses in mice against HIV by intramuscular inoculation with a cloned, genomic (unspliced) HIV gene. However, the level of immune responses achieved in these studies was very low. In addition, the Wang et al., DNA construct utilized an essentially genomic piece of HIV encoding contiguous Tat/rev-gp160-Tat/rev coding sequences. As is described in detail below, this is a suboptimal system for obtaining high-level expression of the gp160. It also is potentially dangerous because expression of Tat contributes to the progression of Kaposi's Sarcoma.

WO 93/17706 describes a method for vaccinating an animal against a virus, wherein carrier particles were coated with a gene construct and the coated particles are accelerated into cells of an animal. In regard to HIV, essentially the entire genome, minus the long terminal repeats, was proposed to be used. That method represents substantial risks for recipients. It is generally believed that constructs of HIV should contain less than about 50% of the HIV genome to ensure safety of the vaccine; this ensures that enzymatic moieties and viral regulatory proteins, many of which have unknown or poorly understood functions have been eliminated. Thus, a number of problems remain if a useful human HIV vaccine is to emerge from the gene-delivery technology.

The instant invention contemplates any of the known methods for introducing polynucleotides into living tissue to induce expression of proteins. However, this invention provides a novel immunogen for introducing HIV and other proteins into the antigen processing pathway to efficiently generate HIV-specific CTLs and antibodies. The pharmaceutical is effective as a vaccine to induce both cellular and humoral anti-HIV and HIV neutralizing immune responses. In the instant invention, the problems noted above are addressed and solved by the provision of polynucleotide immunogens which, when introduced into an animal, direct the efficient expression of HIV proteins and epitopes without the attendant risks associated with those methods. The immune responses thus generated are effective at recognizing HIV, at inhibiting replication of HIV, at identifying and killing cells infected with HIV, and are cross-reactive against many HIV strains.

The codon pairings of organisms are highly nonrandom, and differ from organism to organism. This information is used to construct and express altered or synthetic genes having desired levels of translational efficiency, to determine which regions in a genome are protein coding regions, to introduce translational pause sites into heterologous genes, and to ascertain relationship or ancestral origin of nucleotide sequences.

The expression of foreign heterologous genes in transformed organisms is now commonplace. A large number of mammalian genes, including, for example, murine and human genes, have been successfully inserted into single celled organisms. Standard techniques in this regard include introduction of the foreign gene to be expressed into a vector such as a plasmid or a phage and utilizing that vector to insert the gene into an organism. The native promoters for such genes are commonly replaced with strong promoters compatible with the host into which the gene is inserted. Protein sequencing machinery permits elucidation of the amino acid sequences of even minute quantities of native protein. From these amino acid sequences, DNA sequences coding for those proteins can be inferred. DNA synthesis is also a rapidly developing art, and synthetic genes corresponding to those inferred DNA sequences can be readily constructed.

Despite the burgeoning knowledge of expression systems and recombinant DNA, significant obstacles remain when one attempts to express a foreign or synthetic gene in an organism. Many native, active proteins, for example, are glycosylated in a manner different from that which occurs when they are expressed in a foreign host. For this reason, eukaryotic hosts such as yeast may be preferred to bacterial hosts for expressing many mammalian genes. The glycosylation problem is the subject of continuing research.

Another problem is more poorly understood. Often translation of a synthetic gene, even when coupled with a strong promoter, proceeds much less efficiently than would be expected. The same is frequently true of exogenous genes foreign to the expression organism. Even when the gene is transcribed in a sufficiently efficient manner that recoverable quantities of the translation product are produced, the protein is often inactive or otherwise different in properties from the native protein.

It is recognized that the latter problem is commonly due to differences in protein folding in various organisms. The solution to this problem has been elusive, and the mechanisms controlling protein folding are poorly understood.

The problems related to translational efficiency are believed to be related to codon context effects. The protein coding regions of genes in all organisms are subject to a wide variety of functional constraints, some of which depend on the requirement for encoding a properly functioning protein, as well as appropriate translational start and stop signals. However, several features of protein coding regions have been discerned which are not readily understood in terms of these constraints. Two important classes of such features are those involving codon usage and codon context.

It is known that codon utilization is highly biased and varies considerably between different organisms. Codon usage patterns have been shown to be related to the relative abundance of tRNA isoacceptors. Genes encoding proteins of high versus low abundance show differences in their codon preferences. The possibility that biases in codon usage alter peptide elongation rates has been widely discussed. While differences in codon use are associated with differences in translation rates, direct effects of codon choice on translation have been difficult to demonstrate. Other proposed constraints on codon usage patterns include maximizing the fidelity of translation and optimizing the kinetic efficiency of protein synthesis.

Apart from the non-random use of codons, considerable evidence has accumulated that codon/anticodon recognition is influenced by sequences outside the codon itself, a phenomenon termed "codon context." There exists a strong influence of nearby nucleotides on the efficiency of suppression of nonsense codons as well as missense codons. Clearly, the abundance of suppresser activity in natural bacterial populations, as well as the use of "termination" codons to encode selenocysteine and phosphoserine require that termination be context-dependent. Similar context effects have been shown to influence the fidelity of translation, as well as the efficiency of translation initiation.

Statistical analyses of protein coding regions of *E. coli* demonstrate another manifestation of "codon context." The presence of a particular codon at one position strongly influences the frequency of occurrence of certain nucleotides in neighboring codons, and these context constraints differ markedly for genes expressed at high versus low levels. Although the context effect has been recognized, the predictive value of the statistical rules relating to preferred nucleotides adjacent to codons is relatively low. This has limited the utility of such nucleotide preference data for selecting codons to effect desired levels of translational efficiency.

The advent of automated nucleotide sequencing equipment has made available large quantities of sequence data for a wide variety of organisms. Understanding those data presents substantial difficulties. For example, it is important to identify the coding regions of the genome in order to relate the genetic sequence data to protein sequences. In addition, the ancestry of the genome of certain organisms is of substantial interest. It is known that genomes of some organisms are of mixed ancestry. Some sequences that are viral in origin are now stably incorporated into the genome of eukaryotic organisms. The viral sequences themselves may have originated in another substantially unrelated species. An understanding of the ancestry of a gene can be important in drawing proper analogies between related genes and their translation products in other organisms.

There is a need for a better understanding of codon context effects on translation, and for a method for determining the appropriate codons for any desired translational effect. There is also a need for a method for identifying coding regions of the genome from nucleotide sequence data. There is also a need for a method for controlling protein folding and for insuring that a foreign gene will fold appropriately when expressed in a host. Genes altered or constructed in accordance with desired translational efficiencies would be of significant worth.

Another aspect of the practice of recombinant DNA techniques for the expression by microorganisms of proteins of industrial and pharmaceutical interest is the phenomenon of "codon preference". While it was earlier noted that the existing machinery for gene expression in genetically transformed host cells will "operate" to construct a given desired product, levels of expression attained in a microorganism can be subject to wide variation, depending in part on specific alternative forms of the amino acid-specifying genetic code present in an inserted exogenous gene. A "triplet" codon of four possible nucleotide bases can exist in 64 variant forms. That these forms provide the message for only 20 different amino acids (as well as transcription initiation and termination) means that some amino acids can be coded for by more than one codon. Indeed, some amino acids have as many as six "redundant", alternative codons while some others have a single, required codon. For reasons not completely understood, alternative codons are not at all uniformly present in the endogenous DNA of differing types of cells and there appears to exist variable natural hierarchy or "preference" for certain codons in certain types of cells.

As one example, the amino acid leucine is specified by any of six DNA codons including CTA, CTC, CTG, CTT, TTA, and TTG (which correspond, respectively, to the mRNA codons, CUA, CUC, CUG, CUU, UUA and UUG). Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally held that the likelihood of obtaining high levels of expression of a leucine-rich polypeptide by an E. coli host will depend to some extent on the frequency of codon use. For example, a gene rich in TTA codons will in all probability be poorly expressed in E. coli, whereas a CTG rich gene will probably highly express the polypeptide. Similarly, when yeast cells are the projected transformation host cells for expression of a leucine-rich polypeptide, a preferred codon for use in an inserted DNA would be TTA.

The implications of codon preference phenomena on recombinant DNA techniques are manifest, and the phenomenon may serve to explain many prior failures to achieve high expression levels of exogenous genes in successfully transformed host organisms-a less "preferred" codon may be repeatedly present in the inserted gene and the host cell machinery for expression may not operate as efficiently. This phenomenon suggests that synthetic genes which have been designed to include a projected host cell's preferred codons provide a preferred form of foreign genetic material for practice of recombinant DNA techniques.

The diversity of function that typifies eukaryotic cells depends upon the structural differentiation of their membrane boundaries. To generate and maintain these structures, proteins must be transported from their site of synthesis in the endoplasmic reticulum to predetermined destinations throughout the cell. This requires that the trafficking proteins display sorting signals that are recognized by the molecular machinery responsible for route selection located at the access points to the main trafficking pathways. Sorting decisions for most proteins need to be made only once as they traverse their biosynthetic pathways since their final destination, the cellular location at which they perform their function, becomes their permanent residence.

Maintenance of intracellular integrity depends in part on the selective sorting and accurate transport of proteins to their correct destinations. Over the past few years the dissection of the molecular machinery for targeting and localization of proteins has been studied vigorously. Defined sequence motifs have been identified on proteins which can act as 'address labels'. Leader or signal peptides such as that from the tissue-specific plasminogen activator protein, tPA, serve to transport a protein into the cellular secretory pathway through the endoplasmic reticulum and golgi apparatus. A number of sorting signals have been found associated with the cytoplasmic domains of membrane proteins such as di-Leucine amino acid motifs or tyrosine-based sequences that can direct proteins to lysosomal compartments. For HIV, transport and extrusion from the cell of viral particles depend upon myristoylation of glycine residue number two at the amino terminus of gag.

SUMMARY OF THE INVENTION

Synthetic DNA molecules encoding HIV gag and modifications of HIV gag are provided. The codons of the synthetic molecules include the projected host cell's preferred codons. The synthetic molecules provide preferred forms of foreign genetic material. The synthetic molecules may be used as a polynucleotide vaccine which provides effective immunoprophylaxis against HIV infection through neutralizing antibody and cell-mediated immunity. This invention provides polynucleotides which, when directly introduced into a vertebrate in vivo including mammals such as primates and humans, induce the expression of encoded proteins within the animal.

DETAILED DESCRIPTION OF THE INVENTION

Synthetic DNA molecules encoding HIV gag and synthetic DNA molecules encoding modified forms of HIV gag are provided. The colons of the synthetic molecules are designed so as to use the codons preferred by the projected host cell. The synthetic molecules may be used as a polynucleotide vaccine which provides effective immunoprophylaxis against HIV infection through neutralizing antibody and cell-mediated immunity. The synthetic molecules may be used as an immunogenic composition. This invention provides polynucleotides which, when directly introduced into a vertebrate in vivo, including mammals such as primates and humans, induce the expression of encoded proteins within the animal.

As used herein, a polynucleotide is a nucleic acid which contains essential regulatory elements such that upon introduction into a living, vertebrate cell, it is able to direct the cellular machinery to produce translation products encoded by the genes comprising the polynucleotide. In one embodiment of the invention, the polynucleotide is a polydeoxyribonucleic acid comprising at least one HIV gene operatively linked to a transcriptional promoter. In another embodiment of the invention, the polynucleotide vaccine (PNV) comprises polyribonucleic acid encoding at least one HIV gene which is amenable to translation by the eukaryotic cellular machinery (ribosomes, tRNAs, and other translation factors). Where the protein encoded by the polynucleotide is one which does not normally occur in that animal except in pathological conditions, (i.e., a heterologous protein) such as proteins associated with human immunodeficiency virus, (HIV), the etiologic agent of acquired immune deficiency syndrome, (AIDS), the animals' immune system is activated to launch a protective immune response. Because these exogenous proteins are produced by the animals' tissues, the expressed proteins are processed by the major histocompatibility system, MHC, in a fashion analogous to when an actual infection with the related organism (HIV) occurs. The result, as shown in this disclosure, is induction of immune responses against the cognate pathogen.

Accordingly, the instant inventors have prepared nucleic acids which, when introduced into the biological system induce the expression of HIV proteins and epitopes. The induced antibody response is both specific for the expressed HIV protein, and neutralizes HIV. In addition, cytotoxic T-lymphocytes which specifically recognize and destroy HIV infected cells are induced.

The instant invention provides a method for using a polynucleotide which, upon introduction into mammalian tissue, induces the expression in a single cell, in vivo, of discrete gene products. The instant invention provides a different solution which does not require multiple manipulations of rev dependent HIV genes to obtain rev-independent genes. The rev-independent expression system described herein is useful in its own right and is a system for demonstrating the expression in a single cell in vivo of a single desired gene-product.

Because many of the applications of the instant invention apply to anti-viral vaccination, the polynucleotides are frequently referred to as a polynucleotide vaccine, or PNV. This is not to say that additional utilities of these polynucleotides, in immune stimulation and in anti-tumor therapeutics, are considered to be outside the scope of the invention.

In one embodiment of this invention, a gene encoding an HIV gene product is incorporated in an expression vector. The vector contains a transcriptional promoter recognized by an eukaryotic RNA polymerase, and a transcriptional terminator at the end of the HIV gene coding sequence. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator. The combination of CMVintA-BGH terminator is particularly preferred.

To assist in preparation of the polynucleotides in prokaryotic cells, an antibiotic resistance marker is also preferably included in the expression vector under transcriptional control of a prokaryotic promoter so that expression of the antibiotic does not occur in eukaryotic cells. Ampicillin resistance genes, neomycin resistance genes and other pharmaceutically acceptable antibiotic resistance markers may be used. To aid in the high level production of the polynucleotide by fermentation in prokaryotic organisms, it is advantageous for the vector to contain a prokaryotic origin of replication and be of high copy number. A number of commercially available prokaryotic cloning vectors provide these benefits. It is desirable to remove non-essential DNA sequences. It is also desirable that the vectors not be able to replicate in eukaryotic cells. This minimizes the risk of integration of polynucleotide vaccine sequences into the recipients' genome. Tissue-specific promoters or enhancers may be used whenever it is desirable to limit expression of the polynucleotide to a particular tissue type.

In one embodiment, the expression vector pnRSV is used, wherein the Rous Sarcoma Virus (RSV) long terminal repeat (LTR) is used as the promoter. In another embodiment, V1, a mutated pBR322 vector into which the CMV promoter and the BGH transcriptional terminator were cloned is used. In another embodiment, the elements of V1 and pUC19 have been combined to produce an expression vector named V1J. Into V1J or another desirable expression vector is cloned an HIV gene, such as gp120, gp41, gp160, gag, pol, env, or any other HIV gene which can induce anti-HIV immune responses. In another embodiment, the ampicillin resistance gene is removed from V1J and replaced with a neomycin resistance gene, to generate V1J-neo into different HIV genes have been cloned for use according to this invention. In another embodiment, the vector is V1Jns, which is the same as V1Jneo except that a unique Sfi1 restriction site has been engineered into the single Kpn1 site at position 2114 of V1J-neo. The incidence of Sfi1 sites in human genomic DNA is very low (approximately 1 site per 100,000 bases). Thus, this vector allows careful monitoring for expression vector integration into host DNA, simply by Sfi1 digestion of extracted genomic DNA. In a further refinement, the vector is V1R. In this vector, as much non-essential DNA as possible was "trimmed" from the vector to produce a highly compact vector. This vector is a derivative of V1Jns. This vector allows larger inserts to be used, with less concern that undesirable sequences are encoded and optimizes uptake by cells.

One embodiment of this invention incorporates genes encoding HIV gag from laboratory adapted strains of HIV such as IIIB or CAM-1. Those skilled in the art will recognize that the use of genes from other strains of HIV-1 or HIV-2 strains having analogous function to the genes from HIV-1 would be expected to generate immune responses analogous to those described herein for HIV-1 constructs. The cloning and manipulation methods for obtaining these genes are known to those skilled in the art.

Sequences for many genes of many HIV strains are now publicly available on GENBANK and such primary, field isolates of HIV are available from the National Institute of Allergy and Infectious Diseases (NIAID) which has contracted with Quality Biological, Inc., [7581 Lindbergh Drive, Gaithersburg, Md. 20879] to make these strains available. Such strains are also available from the World Health Organization (WHO) [Network for HIV Isolation and Characterization, Vaccine Development Unit, Office of Research, Global Programme on AIDS, CH-1211 Geneva 27, Switzerland]. From this work those skilled in the art will recognize that one of the utilities of the instant invention is to provide a system for in vivo as well as in vitro testing and analysis so that a correlation of HIV sequence diversity with serology of HIV neutralization, as well as other parameters can be made. Incorporation of genes from primary isolates of HIV strains provides an immunogen which induces immune responses against clinical isolates of the virus and thus meets a need as yet unmet in the field. Furthermore, as the virulent isolates change, the immunogen may be modified to reflect new sequences as necessary.

To keep the terminology consistent, the following convention is followed herein for describing polynucleotide immunogen constructs: "Vector name-HIV strain-gene-additional elements". The additional elements that are added to the construct are described in further detail below. As the etiologic strain of the virus changes, the precise gene which is optimal for incorporation in the pharmaceutical may be changed. However, as is demonstrated below, because CTL responses are induced which are capable of protecting against heterologous strains, the strain variability is less critical in the immunogen and vaccines of this invention, as compared with the whole virus or subunit polypeptide based vaccines. In addition, because the pharmaceutical is easily manipulated to insert a new gene, this is an adjustment which is easily made by the standard techniques of molecular biology.

The term "promoter" as used herein refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers."

The term "leader" as used herein refers to a DNA sequence at the 5' end of a structural gene which is transcribed along with the gene. The leader usually results in the protein having an N-terminal peptide extension sometimes called a pro-sequence. For proteins destined for either secretion to the extracellular medium or a membrane, this signal sequence, which is generally hydrophobic, directs the protein into endoplasmic reticulum from which it is discharged to the appropriate destination.

The term "intron" as used herein refers to a section of DNA occurring in the middle of a gene which does not code for an amino acid in the gene product. The precursor RNA of the intron is excised and is therefore not transcribed into mRNA nor translated into protein.

The term "cassette" refers to the sequence of the present invention which contains the nucleic acid sequence which is to be expressed. The cassette is similar in concept to a cassette tape. Each cassette will have its own sequence. Thus by interchanging the cassette the vector will express a different sequence. Because of the restrictions sites at the 5' and 3' ends, the cassette can be easily inserted, removed or replaced with another cassette.

The term "3' untranslated region" or "3' UTR" refers to the sequence at the 3' end of a structural gene which is usually transcribed with the gene. This 3' UTR region usually contains the poly A sequence. Although the 3' UTR is transcribed from the DNA it is excised before translation into the protein.

The term "Non-Coding Region" or "NCR" refers to the region which is contiguous to the 3' UTR region of the structural gene. The NCR region contains a transcriptional termination signal.

The term "restriction site" refers to a sequence specific cleavage site of restriction endonucleases.

The term "vector" refers to some means by which DNA fragments can be introduced into a host organism or host tissue. There are various types of vectors including plasmid, bacteriophages and cosmids.

The term "effective amount" means sufficient PNV is injected to produce the adequate levels of the polypeptide. One skilled in the art recognizes that this level may vary.

To provide a description of the instant invention, the following background on HIV is provided. The human immunodeficiency virus has a ribonucleic acid (RNA) genome. This RNA genome must be reverse transcribed according to methods known in the art in order to produce a cDNA copy for cloning and manipulation according to the methods taught herein. At each end of the genome is a long terminal repeat which acts as a promoter. Between these termini, the genome encodes, in various reading frames, gag-pol-env as the major gene products: gag is the group specific antigen; pol is the reverse transcriptase, or polymerase; also encoded by this region, in an alternate reading frame, is the viral protease which is responsible for post-translational processing, for example, of gp160 into gp120 and gp41; env is the envelope protein; vif is the virion infectivity factor; rev is the regulator of virion protein expression; nef is the negative regulatory factor; vpu is the virion productivity factor "u"; tat is the trans-activator of transcription; vpr is the viral protein r. The function of each of these elements has been described.

In one embodiment of this invention, a gene encoding an HIV gag protein is directly linked to a transcriptional promoter. However, expression of gag is repressed in the absence of rev due to non-export from the nucleus of non-spliced genes. For an understanding of this system, the life cycle of HIV must be described in further detail.

Figure 1:
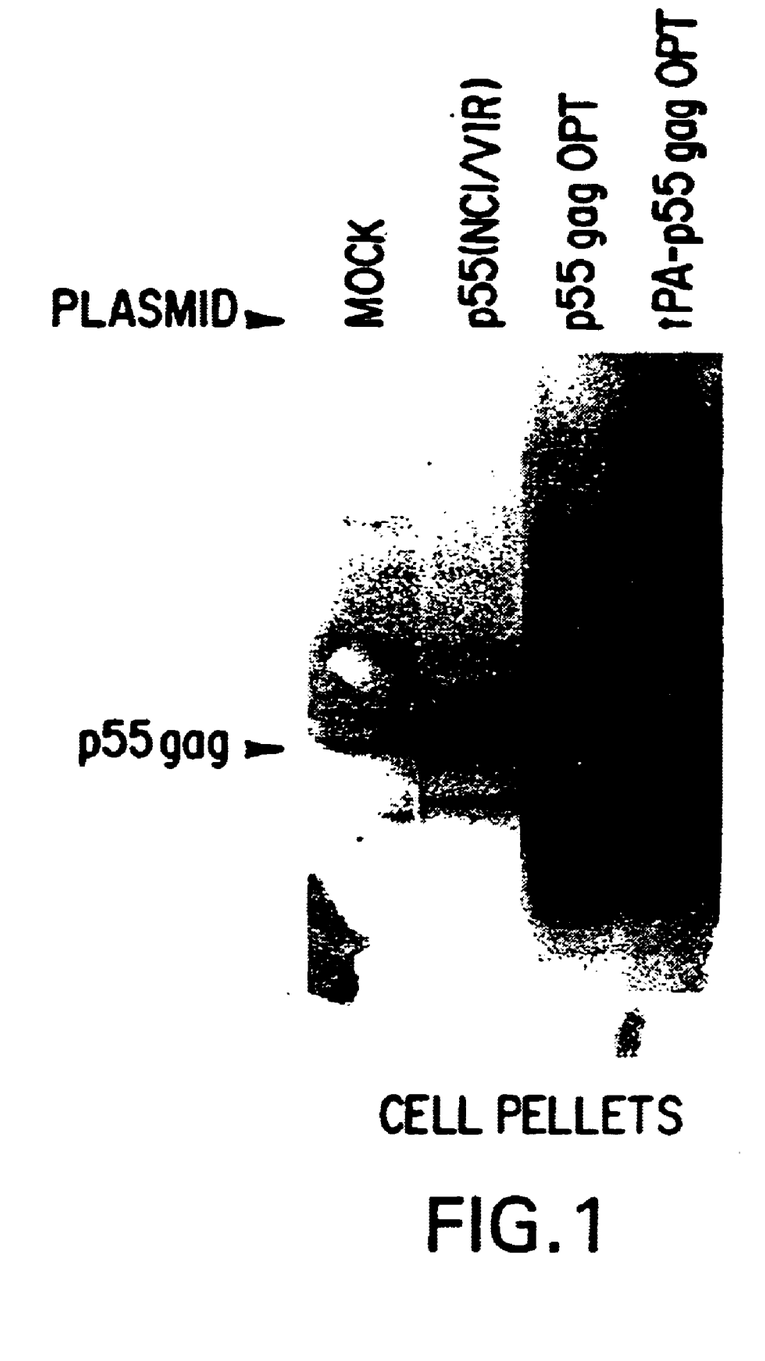
FIG. 1 shows the relative expression of gag and tPA gag in 293 cell line transfectants after transfection with HIV gag DNA.
Figure 2:
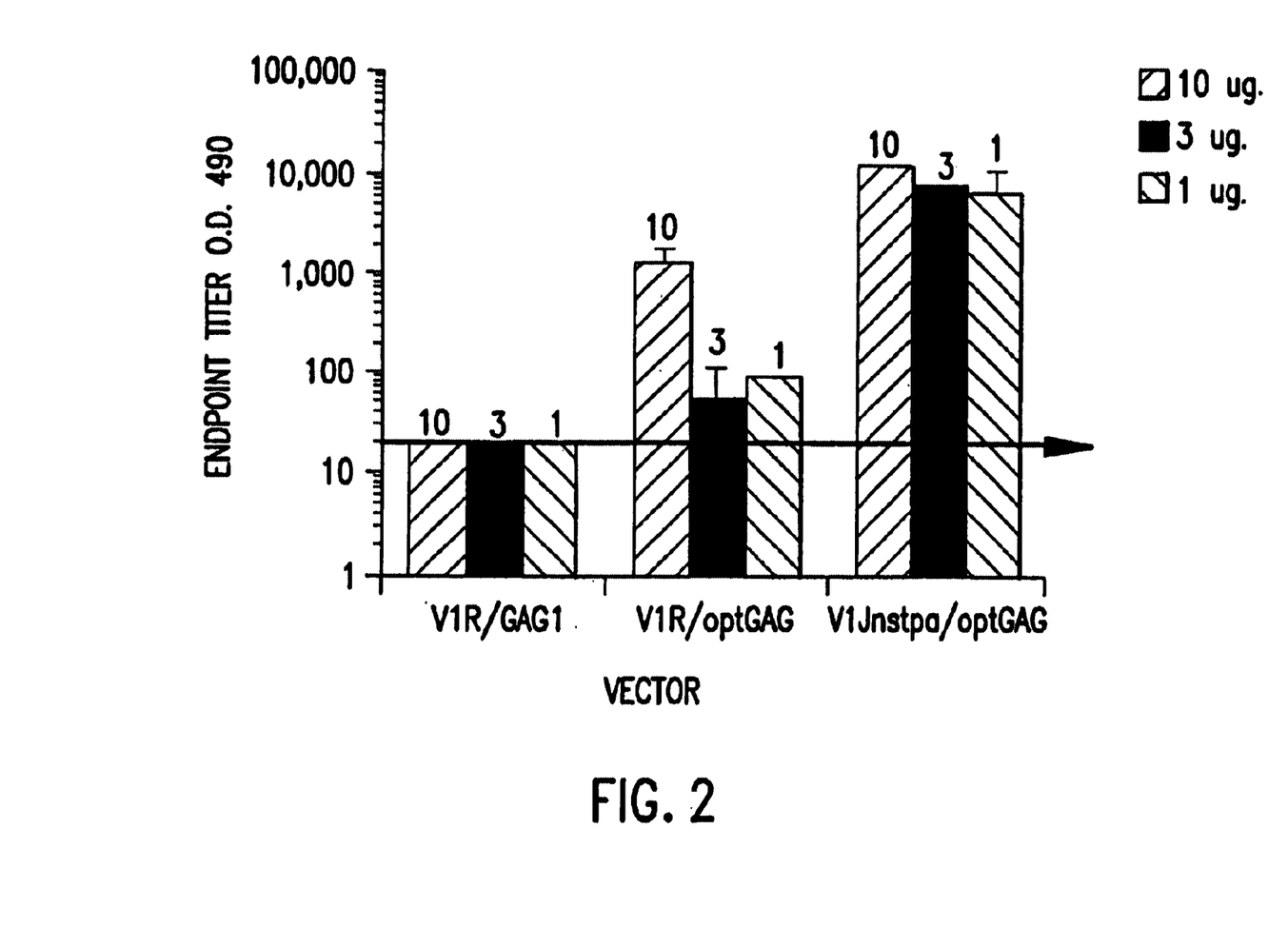
FIG. 2 shows optimized HIV gag and tPA-gag DNA vaccine mediated serum anti-gag responses in mice.
Figure 3A:
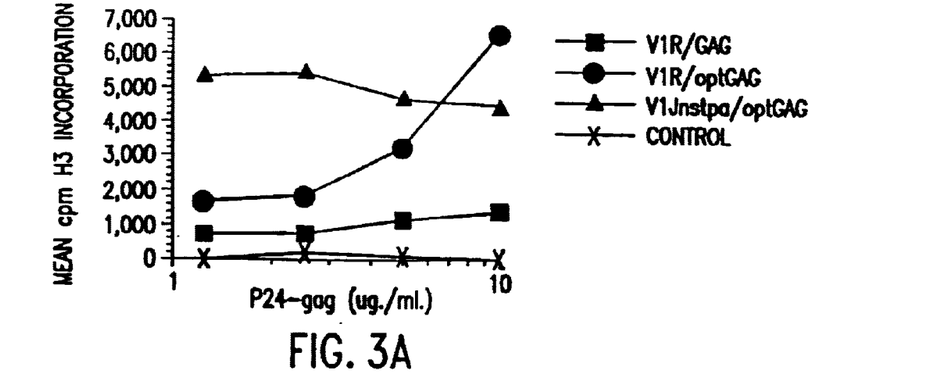
FIG. 3 shows anti-gag CTL responses of splenocytes obtained from mice following vaccination with optimized HIV gag or tPA-gag DNA.
Figure 3B:
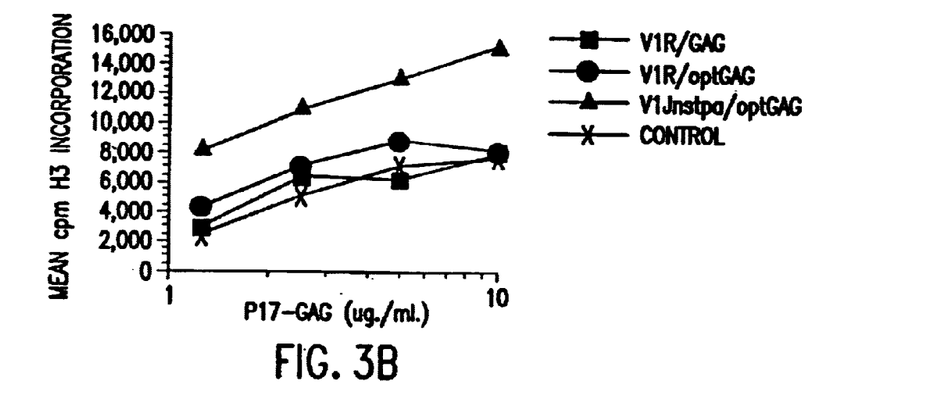
Figure 3C:
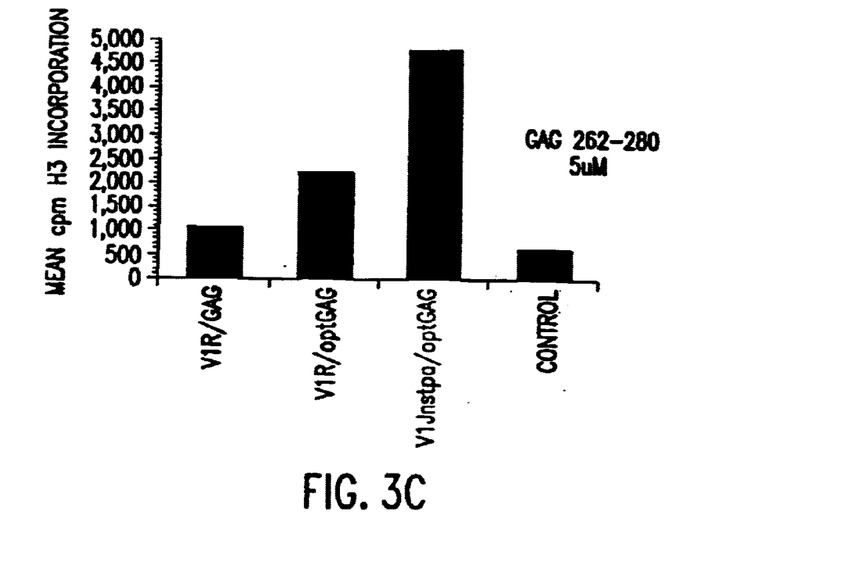
Figure 4:
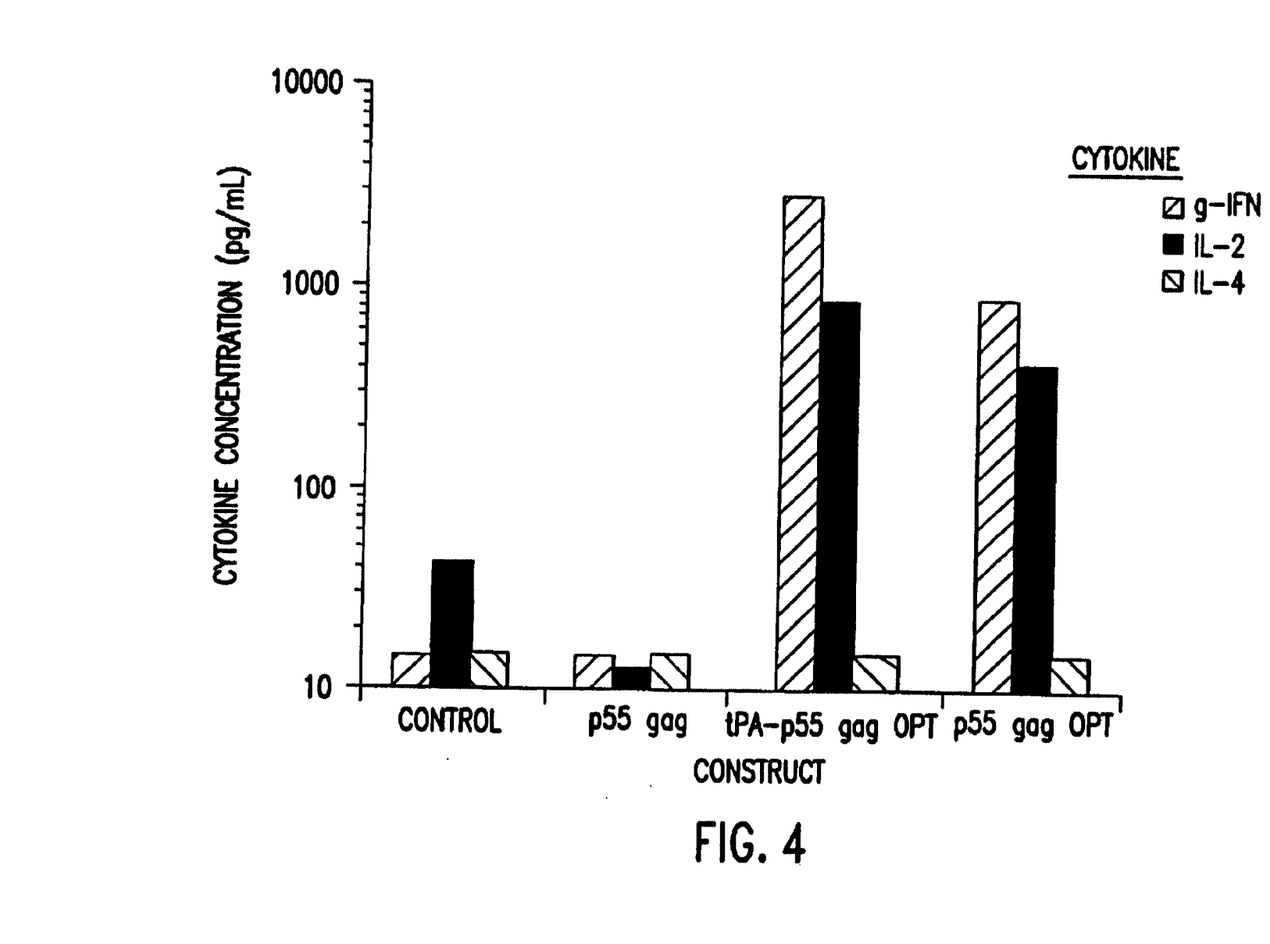
FIG. 4 shows gag antigen-specific cytokine secretion of splenocytes obtained from mice following vaccination with optimized HIV gag or tPA-gag DNA.
Figure 5:
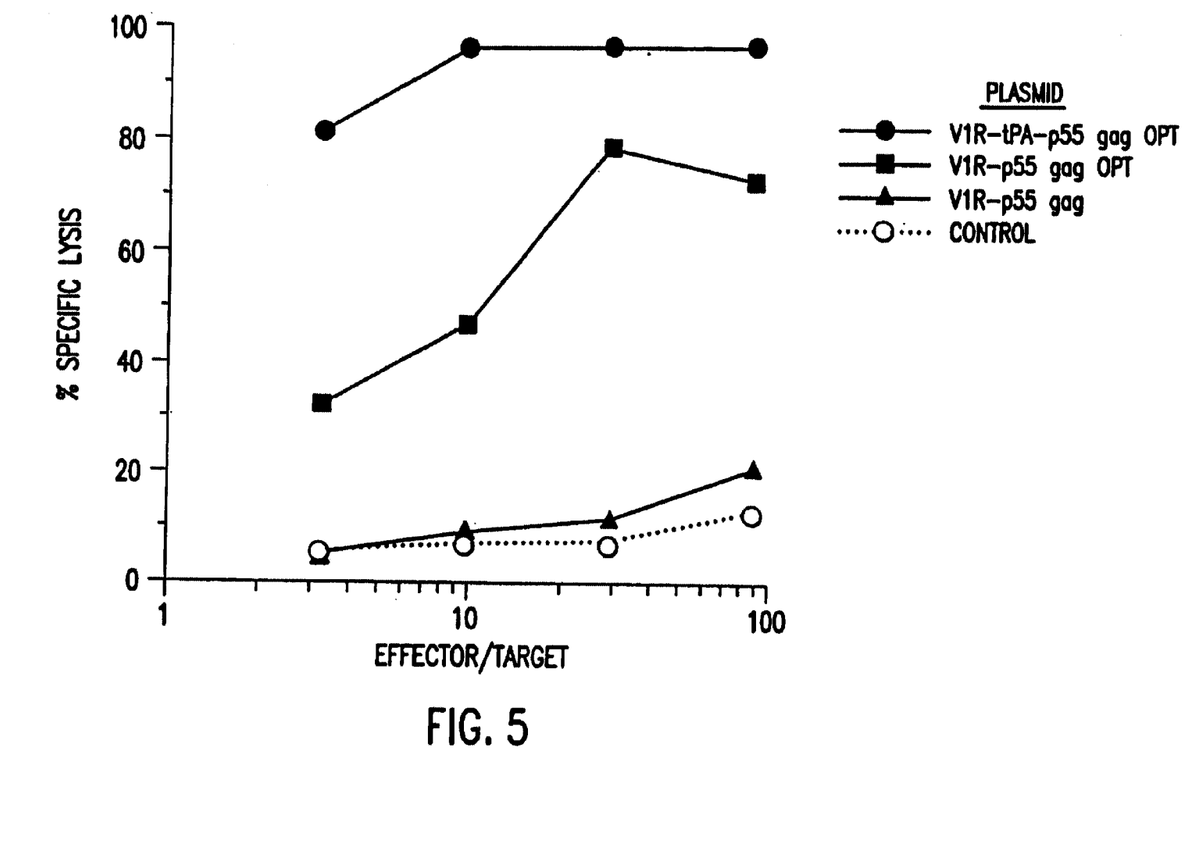
FIG. 5 shows anit-HIV gag CTL from mice vaccinated with HIV p55 gag DNAs.

In the life cycle of HIV, upon infection of a host cell, HIV RNA genome is reverse-transcribed into a proviral DNA which integrates into host genomic DNA as a single transcriptional unit. The LTR provides the promoter which transcribes HIV genes from the 5' to 3' direction (gag, pol, env), to form an unspliced transcript of the entire genome. The unspliced transcript functions as the mRNA from which gag and pol are translated, while limited splicing must occur for translation of env encoded genes. For the regulatory gene product rev to be expressed, more than one splicing event must occur because in the genomic setting, rev and env, as is shown in FIG. 1, overlap. In order for transcription of env to occur, rev transcription must stop, and vice versa. In addition, the presence of rev is required for export of unspliced RNA from the nucleus. For rev to function in this manner, however, a rev responsive element (RRE) must be present on the transcript [Malim et al., Nature 388:254–257 (1989)].

In the polynucleotide vaccine of this invention, the obligatory splicing of certain HIV genes is eliminated by providing fully spliced genes (i.e.: the provision of a complete open reading frame for the desired gene product without the need for switches in the reading frame or elimination of noncoding regions; those of ordinary skill in the art would recognize that when splicing a particular gene, there is some latitude in the precise sequence that results; however so long as a functional coding sequence is obtained, this is acceptable). Thus, in one embodiment, the entire coding sequence for gag is spliced such that no intermittent expression of each gene product is required.

The dual humoral and cellular immune responses generated according to this invention are particularly significant to inhibiting HIV infection, given the propensity of HIV to mutate within the population, as well as in infected individuals. In order to formulate an effective protective vaccine for HIV it is desirable to generate both a multivalent antibody response for example to gp160 (env is approximately 80% conserved across various HIV-1, clade B strains, which are the prevalent strains in US human populations), the principal neutralization target on HIV, as well as cytotoxic T cells reactive to the conserved portions of gp160 and, internal viral proteins encoded by gag. We have made an HIV vaccine comprising gp160 genes selected from common laboratory strains; from predominant, primary viral isolates found within the infected population; from mutated gp160s designed to unmask cross-strain, neutralizing antibody epitopes; and from other representative HIV genes such as the gag and pol genes (~95% conserved across HIV isolates.

Virtually all HIV seropositive patients who have not advanced towards an immunodeficient state harbor anti-gag CTLs while about 60% of these patients show cross-strain, gp160-specific CTLs. The amount of HIV specific CTLs found in infected individuals that have progressed on to the disease state known as AIDS, however, is much lower, demonstrating the significance of our findings that we can induce cross-strain CTL responses.

Immune responses induced by our env and gag polynucleotide vaccine constructs are demonstrated in mice and primates. Monitoring antibody production to env in mice allows confirmation that a given construct is suitably immunogenic, i.e., a high proportion of vaccinated animals show an antibody response. Mice also provide the most facile animal model suitable for testing CTL induction by our constructs and are therefore used to evaluate whether a particular construct is able to generate such activity. Monkeys (African green, rhesus, chimpanzees) provide additional species including primates for antibody evaluation in larger, non-rodent animals. These species are also preferred to mice for antisera neutralization assays due to high levels of endogenous neutralizing activities against retroviruses observed in mouse sera. These data demonstrate that sufficient immunogenicity is engendered by our vaccines to achieve protection in experiments in a chimpanzee/$HIV_{IIIB}$ challenge model based upon known protective levels of neutralizing antibodies for this system. However, the currently emerging and increasingly accepted definition of protection in the scientific community is moving away from so-called "sterilizing immunity", which indicates complete protection from HIV infection, to prevention of disease. A number of correlates of this goal include reduced blood viral titer, as measured by PCR, HIV reverse transcriptase activity, by infectivity of samples of serum, by ELISA assay of p24 or other HIV antigen concentration in blood, increased CD4+ T-cell concentration, and by extended survival rates [see, for example, Cohen, J., Science 262:1820–1821, 1993, for a discussion of the evolving definition of anti-HIV vaccine efficacy]. The immunogens of the instant invention also generate neutralizing immune responses against infectious (clinical, primary field) isolates of HIV.

An ELISA assay is used to determine whether optimized gag vaccine vectors expressing either secreted tPA-gag or native gag are efficacious for production of gag-specific antibodies. Initial in vitro characterization of gag expression by our vaccination vectors is provided by immunoblot analysis of optimized gag transfected cell lysates. These data confirm and quantitate gag expression using anti-HIV antisera to visualize transfectant cell gag expression.

Generation of CTL Responses. Viral proteins which are synthesized within cells give rise to MHC I-restricted CTL responses. Each of these proteins elicits CTL in seropositive patients. Our vaccines also are able to elicit CTL in mice and rhesus monkeys. The immunogenetics of mouse strains are conducive to such studies, as demonstrated with influenza NP, [see Ulmer et al., Science 259:1745–1749, 1993]. Several epitopes have been defined for the HIV proteins env, rev, nef and gag (Frankel, F. R., et al., J. Immunol. 155, 4775–82 (1995) in Balb/c mice, thus facilitating in vitro CTL culture and cytotoxicity assays. Alternatively, the entire gene encoding gp160, gp120, pol, or gag could be used. For additional review on this subject, see for example, (HIV Molecular Immunology Database 1995, Korber et al. eds., Los Alamos National Laboratory, Los Alamos, N. Mex., USA).As used herein, T-cell effector function is associated with mature T-cell phenotype, for example, cytotoxicity, cytokine secretion for B-cell activation, and/or recruitment or stimulation of macrophages and neutrophils.

Measurement of $T_H$ Activities. Spleen cell cultures derived from vaccinated animals are tested for recall to specific antigens by addition of either recombinant protein or peptide epitopes. Activation of T cells by such antigens, presented by accompanying splenic antigen presenting cells, APCs, is monitored by proliferation of these cultures or by cytokine production. The pattern of cytokine production also allows classification of $T_H$ response as type 1 or type 2. Because dominant $T_H2$ responses appear to correlate with the exclusion of cellular immunity in immunocompromised seropositive patients, it is possible to define the type of response engendered by a given PNV in patients, permitting manipulation of the resulting immune responses.

Based upon the above immunologic studies, it is predictable that our vaccines are effective in vertebrates against challenge by virulent HIV. These studies are accomplished in an $HIV_{IIIB}$/chimpanzee challenge model after sufficient vaccination of these animals with a PNV construct, or a cocktail of PNV constructs comprised of $gp160_{IIIB}$, $gag_{IIIB}$, $nef_{IIIB}$ and $REV_{IIIB}$. The IIIB strain is useful in this regard as the chimpanzee titer of lethal doses of this strain has been established. However, the same studies are envisioned using any strain of HIV and the epitopes specific to or heterologous to the given strain. A second vaccination/challenge model, in addition to chimpanzees, is the scid-hu PBL mouse. This model allows testing of the human lymphocyte immune system and our vaccine with subsequent HIV challenge in a mouse host. This system is advantageous as it is easily adapted to use with any HIV strain and it provides evidence of protection against multiple strains of primary field isolates of HIV. A third challenge model utilizes hybrid HIV/SIV viruses (SHIV), some of which have been shown to infect rhesus monkeys and lead to immunodeficiency disease resulting in death [see Li, J., et al., J. AIDS 5:639–646, 1992]. Vaccination of rhesus with our polynucleotide vaccine constructs is protective against subsequent challenge with lethal doses of SHIV.

There are numerous viral and bacterially derived genes which do not utilize codons that are optimized for expression in mammalian cells. Reasons for this include the fact that these microorganisms provide their own polymerases or provide specific proteins or factors to facilitate transcription/translation of their gene products. For bacteria, there may be different relative abundances for specific tRNAs. Clearly in vivo expression of such genes in the context of a DNA vaccine is substantially different.

Representative construct components include (but are not restricted to): HIV env, HIV gag, HIV pol, HIV rev, HIV vpr, and HIV nef. Genes encoding antigens expressed by pathogens other than HIV, such as, but not limited to, influenza virus nucleoprotein, hemagglutinin, matrix, neuraminidase, and other antigenic proteins; herpes simplex virus genes; human papillomavirus genes; tuberculosis antigens; hepatitis A, B, or C virus antigens.

The protective efficacy of polynucleotide HIV immunogens against subsequent viral challenge is demonstrated by immunization with the non-replicating plasmid DNA of this invention. This is advantageous since no infectious agent is involved, assembly of virus particles is not required, and determinant selection is permitted. Furthermore, because the sequence of gag and protease and several of the other viral gene products is conserved among various strains of HIV, protection against subsequent challenge by a virulent strain of HIV that is homologous to, as well as strains heterologous to the strain from which the cloned gene is obtained, is enabled.

The invention offers a means to induce cross-strain protective immunity without the need for self-replicating agents or adjuvants. In addition, immunization with the instant polynucleotides offers a number of other advantages. This approach to vaccination should be applicable to tumors as well as infectious agents, since the CD8+ CTL response is important for both pathophysiological processes [K. Tanaka et al, Annu. Rev. Immunol. 6, 359 (1988)]. Therefore, eliciting an immune response against a protein crucial to the transformation process may be an effective means of cancer protection or immunotherapy. The generation of high titer antibodies against expressed proteins after injection of viral protein and human growth hormone DNA suggests that this is a facile and highly effective means of making antibody-based vaccines, either separately or in combination with cytotoxic T-lymphocyte vaccines targeted towards conserved antigens.

The ease of producing and purifying DNA constructs compares favorably with traditional methods of protein purification, thus facilitating the generation of combination vaccines. Accordingly, multiple constructs, for example encoding gp160, gp120, gp41, gag, or any other HIV gene may be prepared, mixed and co-administered. Because protein expression is maintained following DNA injection, the persistence of B- and T-cell memory may be enhanced, thereby engendering long-lived humoral and cell-mediated immunity.

Standard techniques of molecular biology for preparing and purifying DNA constructs enable the preparation of the DNA immunogens of this invention. While standard techniques of molecular biology are therefore sufficient for the production of the products of this invention, the specific constructs disclosed herein provide novel polynucleotide immunogens which surprisingly produce cross-strain and primary HIV isolate neutralization, a result heretofore unattainable with standard inactivated whole virus or subunit protein vaccines.

The amount of expressible DNA or transcribed RNA to be introduced into a vaccine recipient will depend on the strength of the transcriptional and translational promoters used and on the immunogenicity of the expressed gene product. In general, an immunologically or prophylactically effective dose of about 1 ng to 100 mg, and preferably about 10 $\mu$g to 300 $\mu$g is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided. Following vaccination with HIV polynucleotide immunogen, boosting with HIV protein immunogens such as gp160, gp120, and gag gene products is also contemplated. Parenteral administration, such as intravenous, intramuscular, subcutaneous or other means of administration of interleukin-12 protein, concurrently with or subsequent to parenteral introduction of the PNV of this invention is also advantageous.

The polynucleotide may be naked, that is, unassociated with any proteins, adjuvants or other agents which impact on the recipients' immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

The following examples are offered by way of illustration and are not intended to limit the invention in any manner.

EXAMPLE 1

Heterologous Expression of HIV Late Gene Products

HIV structural genes such as env and gag require expression of the HIV regulatory gene, rev, in order to efficiently produce full-length proteins. We have found that rev-dependent expression of gag yielded low levels of protein and that rev itself may be toxic to cells. Although we achieved relatively high levels of rev-dependent expression of gp160 in vitro this vaccine elicited low levels of antibodies to gp160 following in vivo immunization with rev/gp160 DNA. This may result from known cytotoxic effects of rev as well as increased difficulty in obtaining rev function in myotubules containing hundreds of nuclei (rev protein needs to be in the same nucleus as a rev-dependent transcript for gag or env protein expression to occur). However, it has been possible to obtain rev-independent expression using selected modifications of the env gene.

In general, our vaccines have utilized primarily HIV (IIIB, MN or CAM-1) env and gag genes for optimization of expression within our generalized vaccination vector, V1Jns, which is comprised of a CMV immediate-early (IE) promoter, BGH polyadenylation site, and a pUC backbone. Varying efficiencies, depending upon how large a gene segment is used (e.g., gp120 vs. gp160), of rev-independent expression may be achieved for env by replacing its native secretory leader peptide with that from the tissue-specific plasminogen activator (tPA) gene and expressing the resulting chimeric gene behind the CMVIE promoter with the CMV intron A As stated previously, we consider realization of the following objectives to be essential to maximize our chances for success with this program: (1) env-based vectors capable of generating stronger neutralizing antibody responses in primates; (2) gag and env vectors which elicit strong T-lymphocyte responses as characterized by CTL and helper effector functions in primates; (3) use of env and gag genes from clinically relevant HIV-1 strains in our vaccines and characterization of the immunologic responses, especially neutralization of primary isolates, they elicit; (4) demonstration of protection in an animal challenge model such as chimpanzee/HIV (IIIB) or rhesus/SHIV using appropriate optimized vaccines; and, (5) determination of the duration of immune responses appropriate to clinical use. Significant progress has been made on the first three of these objectives and experiments are in progress to determine whether our recent vaccination constructs for gp160 and gag will improve upon these initial results.

EXAMPLE 2

Vectors For Vaccine Production

A. V1Jneo Expression Vector

It was necessary to remove the amp$^r$ gene used for antibiotic selection of bacteria harboring V1J because ampicillin may not be used in large-scale fermenters. The amp$^r$ gene from the pUC backbone of V1J was removed by digestion with SspI and Eam1105I restriction enzymes. The remaining plasmid was purified by agarose gel electrophoresis, blunt-ended with T4 DNA polymerase, and then treated with calf intestinal alkaline phosphatase. The commercially available kan$^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the kan$^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. We arbitrarily selected V1Jneo#3, referred to as V1Jneo hereafter, which contains the kan$^r$ gene in the same orientation as the amp$^r$ gene in V1J as the expression construct.

B. VI Jns Expression Vector

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

C. V1Jns-tPA

In order to provide an heterologous leader peptide sequence to secreted and/or membrane proteins, V1Jn was modified to include the human tissue-specific plasminogen activator (tPA) leader. Two synthetic complementary oligomers were annealed and then ligated into V1Jn which had been BglII digested. These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing. Additionally, in order to conform with our consensus optimized vector V1Jns (=V1Jneo with an SfiI site), an SfiI restriction site was placed at the KpnI site within the BGH terminator region of V1Jn-tPA by blunting the KpnI site with T4 DNA polymerase followed by ligation with an SfiI linker (catalogue #1138, New England Biolabs). This modification was verified by restriction digestion and agarose gel electrophoresis.

D. Vector V1R Preparation

In an effort to continue to optimize our basic vaccination vector, we prepared a derivative of V1Jns which was designated as V1R. The purpose for this vector construction was to obtain a minimum-sized vaccine vector, i.e., without unnecessary DNA sequences, which still retained the overall optimized heterologous gene expression characteristics and high plasmid yields that V1J and V1Jns afford. We determined from the literature as well as by experiment that (1) regions within the pUC backbone comprising the E. coli origin of replication could be removed without affecting plasmid yield from bacteria; (2) the 3'-region of the kan$^r$ gene following the kanamycin open reading frame could be removed if a bacterial terminator was inserted in its stead; and, (3) ~300 bp from the 3'- half of the BGH terminator could be removed without affecting its regulatory function (following the original KpnI restriction enzyme site within the BGH element).

V1R was constructed by using PCR to synthesize three segments of DNA from V1Jns representing the CMVintA promoter/BGH terminator, origin of replication, and kanamycin resistance elements, respectively. Restriction enzymes unique for each segment were added to each segment end using the PCR oligomers: SspI and XhoI for CMVintA/BGH; EcoRV and BamHI for the kan$^r$ gene; and, BclI and SalI for the ori$^r$. These enzyme sites were chosen because they allow directional ligation of each of the PCR-derived DNA segments with subsequent loss of each site: EcoRV and SspI leave blunt-ended DNAs which are compatible for ligation while BamHI and BclI leave complementary overhangs as do SalI and XhoI. After obtaining these segments by PCR each segment was digested with the appropriate restriction enzymes indicated above and then ligated together in a single reaction mixture containing all three DNA segments. The 5'-end of the ori$^r$ was designed to include the T2 rho independent terminator sequence that is normally found in this region so that it could provide termination information for the kanamycin resistance gene. The ligated product was confirmed by restriction enzyme digestion (>8 enzymes) as well as by DNA sequencing of the ligation junctions. DNA plasmid yields and heterologous expression using viral genes within V1R appear similar to V1Jns. The net reduction in vector size achieved was 1346 bp (V1Jns=4.86 kb; V1R=3.52 kb).

EXAMPLE 3

Design of Synthetic Gene Segments for Increased gag Gene Expression

Gene segments were converted to sequences having identical translated sequences but with alternative codon usage as defined by R. Lathe in a research article from *J. Molec. Biol.* Vol. 183, pp. 1–12 (1985) entitled "Synthetic Oligonucleotide Probes Deduced from Amino Acid Sequence Data: Theoretical and Practical Considerations". The methodology described below to increase of expression of HIV gag gene segments was based on our hypothesis that the known inability to express this gene efficiently in mammalian cells is a consequence of the overall transcript composition. Thus, using alternative codons encoding the same protein sequence may remove the constraints on expression of gag. The specific codon replacement method employed may be described as follows:

1. Identify placement of codons for proper open reading frame.
2. Compare wild type codon for observed frequency of use by human genes.
3. If codon is not the most commonly employed, replace it with an optimal codon for high expression in human cells.
4. Repeat this procedure until the entire gene segment has been replaced.
5. Inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences.
6. Assemble synthetic gene segments and test for improved expression.

These methods were used to create the following synthetic gene segments for HIV gag creating a gene comprised entirely of optimal codon usage for expression. While the above procedure provides a summary of our methodology for designing codon-optimized genes for DNA vaccines, it is understood by one skilled in the art that similar vaccine efficacy or increased expression of genes may be achieved by minor variations is the procedure or by minor variations in the sequence.

EXAMPLE 4

| I. HIV gag Vaccine Constructs: This is a complete HIV-1 (CAM 1) gag orf comprised of optimal codons. | |
|---|---|
| 1 | AGATCTACCA TGGCTGCTAG GGCTTCTGTG CTGTCTGGTG GTGAGCTGGA (SEQ ID NO:1) |
| 51 | CAAGTGGGAG AAGATCAGGC TGAGGCCTGG TGGCAAGAAG AAGTACAAGC |
| 101 | TAAAGCACAT TGTGTGGGCC TCCAGGGAGC TGGAGAGGTT TGCTGTGAAC |
| 151 | CCTGGCCTGC TGGAGACCTC TGAGGGGTGC AGGCAGATCC TGGGCCAGCT |
| 201 | CCAGCCCTCC CTGCAAACAG GCTCTGAGGA GCTGAGGTCC CTGTACAACA |
| 251 | CAGTGGCTAC CCTGTACTGT CTGCACCACA AGATTGATGT GAAGGACACC |
| 301 | AAGGAGGCCC TGGAGAAGAT TGAGGAGGAG CAGAACAAGT CCAAGAAGAA |
| 351 | GGCCCAGCAG GCTGCTGCTG GCACAGGCAA CTCCAGCCAG GTGTCCCAGA |
| 401 | ACTACCCCAT TGTGCAGAAC CTCCAGGGCC AGATGGTGCA CCAGGCCATC |
| 451 | TCCCCCCGGA CCCTGAATGC CTGGGTGAAG GTGGTGGAGG AGAAGGCCTT |
| 501 | CTCCCCTGAG GTGATCCCCA TGTTCTCTGC CCTGTCTGAG GGTGCCACCC |
| 551 | CCCAGGACCT GAACACCATC CTGAACACAG TCCGGCGCCA TCACGCTGCC |
| 601 | ATCCAGATGC TGAAGGAGAC CATCAATGAG GAGGCTGCTG AGTGGGACAG |
| 651 | GCTGCATCCT GTGCACGCTG GCCCCATTGC CCCCGGCCAG ATGAGGGAGC |
| 701 | CCAGGCGCTC TGACATTGCT GGCACCACCT CCACCCTCCA GGAGCAGATT |
| 751 | GGCTGGATGA CCAACAACCC CCCCATCCCT GTGGGGGAAA TCTACAACAG |
| 801 | GTGCATCATC CTGGGCCTGA ACAAGATTGT GAGGATGTAC TCCCCCACCT |
| 851 | CCATCCTGGA CATCAGGCAG GGCCCCAAGG AGCCCTTCAG GGACTATGTG |
| 901 | GACAGGTTCT ACAAGACCCT GAGGGCTGAG CAGGCCTCCC AGGAGGTGAA |
| 951 | GAACTGGATG ACAGAGACCC TGCTGGTGCA GAATGCCAAC CCTGACTGCA |
| 1001 | AGACCATCCT GAAGGCCCTG GGCCCTGCTG CCACCCTGGA CGAGATGATG |
| 1051 | ACAGCCTGCC AGGGGGTGGG GGGCCCTGGT CACAAGGCCA GGGTGCTGGC |
| 1101 | TGACGCCATG TCCCAGGTGA CCAACTCCGC CACCATCATG ATGCAGAGGG |
| 1151 | GCAACTTCAG GAACCAGAGG AAGACAGTGA AGTGCTTCAA CTGTGGCAAG |
| 1201 | GTGGGCCACA TTGCCAAGAA GTGTAGGGCC CCCAGGAAGA AGGGCTGCTG |
| 1251 | GAAGTGTGGC AAGGAGGGCC ACCAGATGAA GGACTGCAAT GAGAGGCAGG |
| 1301 | CCAACTTCCT GGGCAAAATC TGGCCCTCCC ACAAGGGCAG GCCTGGCAAC |
| 1351 | TTCCTCCAGT CCAGGCCTGA GCCCACAGCC CCTCCCGAGG AGTCCTTCAG |
| 1401 | GTTTGGGGAG GAGAAGACCA CCCCCAGCCA GAAGCAGGAG CCCATTGACA |
| 1451 | ACGAGCTCTA CCCCCTGGCC TCCCTGAGGT CCCTGTTTGG CAACGACCCC |
| 1501 | TCCTCCCAGT AAAATAAAGC CCGGGCAGAT CT |

EXAMPLE 5

In Vitro gag Vaccine Expression

In vitro expression was tested in transfected human rhabdomyosarcoma (RD) or 293 cells for these constructs. Quantitation of gag from transfected 293 cells showed that V1Jns-opt-gag and V1Jns-tPA-opt gag vector produced secreted gag.

EXAMPLE 6

Assay For HIV-gag Cytotoxic T-Lymphocytes

The methods described in this section illustrate the assay as used for vaccinated mice. An essentially similar assay can be used with primates except that autologous B cell lines must be established for use as target cells for each animal. This can be accomplished for humans using the Epstein-Barr virus and for rhesus monkey using the herpes B virus.

Peripheral blood mononuclear cells (PBMC) are derived from either freshly drawn blood or spleen using Ficoll-Hypaque centrifugation to separate erythrocytes from white blood cells. For mice, lymph nodes may be used as well. Effector CTLs may be prepared from the PBMC either by in vitro culture in IL-2 (20 U/ml) and concanavalin A (2 μg/ml) for 6–12 days or by using specific antigen using an equal number of irradiated antigen presenting cells. Specific antigen can consist of either synthetic peptides (9–15 amino acids usually) that are known epitopes for CTL recognition for the MHC haplotype of the animals used, or vaccinia virus constructs engineered to express appropriate antigen. Target cells may be either syngenic or MHC haplotype-matched cell lines which have been treated to present appropriate antigen as described for in vitro stimulation of the CTLs. For Balb/c mice the gag peptide of Paterson (J. Immunol., 1995), was used at 10 μM concentration to restimulate CTL in vitro using irradiated syngenic splenocytes and can be used to sensitize target cells during the cytotoxicity assay at 1–10 μM by incubation at 37° C. for about two hours prior to the assay. For these H-$2^d$ MHC haplotype mice, the murine mastocytoma cell line, P815, provides good target cells. Antigen-sensitized target cells are loaded with Na$^{51}$CrO$_4$, which is released from the interior of the target cells upon killing by CTL, by incubation of targets for 1–2 hours at 37° C. (0.2 mCi for ~5×10$^6$ cells) followed by several washings of the target cells. CTL populations are mixed with target cells at varying ratios of effectors to targets such as 100:1, 50:1, 25:1, etc., pelleted together, and incubated 4–6 hours at 37° C. before harvest of the supernatants which are then assayed for release of radioactivity using a gamma counter. Cytotoxicity is calculated as a percentage of total releasable counts from the target cells (obtained using 0.2% Triton X-100 treatment) from which spontaneous release from target cells has been subtracted.

EXAMPLE 7

Assay For HIV gag Specific Antibodies

ELISA were designed to detect antibodies generated against HIV using either specific recombinant p24 gag protein as substrate antigens. 96 well microtiter plates were coated at 40° C. overnight with recombinant antigen at 2 μg/ml in PBS (phosphate buffered saline) solution using 50 μl/well on a rocking platform. Antigens consisted of recombinant p24 gag (Intracell). Plates were rinsed four times using wash buffer (PBS/0.05% Tween 20) followed by addition of 200 μl/well of blocking buffer (1% Carnation milk solution in PBS/0.05% Tween-20) for 1 hr at room temperature with rocking. Pre-sera and immune sera were diluted in blocking buffer at the desired range of dilutions and 100 μl added per well. Plates were incubated for 1 hr at room temperature with rocking and then washed four times with wash buffer.

Secondary antibodies conjugated with horse radish peroxidase, (anti-rhesus Ig, Southern Biotechnology Associates; anti-mouse and anti-rabbit Igs, Jackson Immuno Research) diluted 1:2000 in blocking buffer, were then added to each sample at 100 μl/well and incubated 1 hr at room temperature with rocking. Plates were washed 4 times with wash buffer and then developed by addition of 100 μl/well of an o-phenylenediamine (o-PD, Calbiochem) solution at 1 mg/ml in 100 mM citrate buffer at pH 4.5. Plates were read for absorbance at 450 nm both kinetically (first ten minutes of reaction) and at 10 and 30 minute endpoints (Thermo-max microplate reader, Molecular Devices).

EXAMPLE 8

T Cell Proliferation Assays

PBMCs are obtained and tested for recall responses to specific antigen as determined by proliferation within the PBMC population. Proliferation is monitored using $^3$H-thymidine which is added to the cell cultures for the last 18–24 hours of incubation before harvest. Cell harvesters retain isotope-containing DNA on filters if proliferation has occurred while quiescent cells do not incorporate the isotope which is not retained on the filter in free form. For either rodent or primate species 4×10$^5$ cells are plated in 96 well microtiter plates in a total of 200 μl of complete media (RPMI/10% fetal calf serum). Background proliferation responses are determined using PBMCs and media alone while nonspecific responses are generated by using lectins such as phytohaemagglutin (PHA) or concanavalin A (ConA) at 1–5 μg/ml concentrations to serve as a positive control. Specific antigen consists of either known peptide epitopes, purified protein, or inactivated virus. Antigen concentrations range from 1–10 μM for peptides and 1–10 μg/ml for protein. Lectin-induced proliferation peaks at 3–5 days of cell culture incubation while antigen-specific responses peak at 5–7 days. Specific proliferation occurs when radiation counts are obtained which are at least three-fold over the media background and is often given as a ratio to background, or Stimulation Index (SI).

EXAMPLE 9

The strategies we employ are designed to induce both cytotoxic T lymphocyte (CTL) and neutralizing antibody responses to HIV, principally directed at the HIV gag (~95% conserved) and env (gp160 or gp120; 70–80% conserved) gene products. gp160 contains the only known neutralizing antibody epitopes on the HIV particle while the importance of anti-env and anti-gag CTL responses are highlighted by the known association of the onset of these cellular immunities with clearance of primary viremia following infection, which occurs prior to the appearance of neutralizing antibodies (Koup et al., *J. Virol.* 68: 4650 (1994)), as well as a role for CTL in maintaining disease-free status. Although HIV is notorious for its genetic diversity we hope to obtain greater breadth of neutralizing antibodies both by including several representative env genes derived from clinical isolates and gp41 (~90% conserved; and contains the more conserved 2F5 neutralization epitope), while the highly conserved gag gene should generate broad cross-strain CTL responses. Because this vaccine strategy generates both strong humoral and cellular immunity against HIV (in nonhuman primates, this approach offers unique advantages compared to other available vaccination strategies for HIV.

A. HIV-1 gag Polynucleotide Vaccine Development

Based upon our experiments for HIV env gene expression utilizing genes comprised of optimal codons for human expression, a synthetic p55 gag gene (opt gag) was designed and synthesized containing optimal codon usage throughout resulting in ~350 silent mutations (of 1500 nt total) and cloned into V1R. A second form of opt gag vector was also constructed which contained the sequence encoding the tPA signal peptide at the NH$_2$-terminus similar to that described above for HIV env and also eliminated a nuclear localization sequence motif located at this position in the wild type gene. This modification was designed to test whether altering the normal intracellular trafficking patterns for gag into the ER/golgi secretory pathway could alter the immunogenicity of the gag DNA vaccine. The addition of the tPA leader peptide to gag caused much higher levels of gag to be secreted and the secreted protein migrated as higher molecular weight form compared to w.t. gag. This indicated that posttranslation modification, probably glycosylation, occurred as a result of modification with the tPA leader peptide.

Mice that had been immunized with either one of the two optimized p55 gag constructs (V1R-opt gag±tPA leader) or V1R-gag (wild-type) were tested for anti-gag peptide CTL responses following one injection (vaccination doses=10, 3.3, or 1 μg/mouse). High levels of anti-gag CTL were generated by both V1R-opt gag DNAs at all doses with V1R-tPA-opt gag giving the highest specific killing (~85% @ E/T=3 with the 1 μg dose). Comparison of cytotoxicity curves at each DNA doses demonstrated that V1R-tPA-opt gag vaccination produced ~100-fold stronger CTL responses than did V1R-gag (wild-type). Overall, immune responses for the three vaccine groups showed the same relative potencies for CTL, T help, and antibody responses (in order from greatest to lowest response): V1R-tPA-opt gag>V1R-opt gag>V1R gag (wild-type). In summary, CTL, humoral and helper T cell responses are much higher for the opt gag constructs, especially with a tPA leader.

EXAMPLE 10

Method of Treatment

A person in need of therapeutic or prophylactic immunization against infection with human immunodeficiency virus is injected with HIV DNA encoding all or part of the env, gag or pol genes or combinations thereof. The injection may be i.p., subcutaneous, intramuscular or intradermal. The HIV DNA may be used as a primer of the immune response or may be used as a booster of the immune response. The injection of DNA may antedate, coincide or follow injection of the person with a pharmaceutical composition comprising inactivated HIV, attenuated HIV, compositions comprising HIV-derived proteins, or combinations thereof.

EXAMPLE 11

Method of Treatment

A person in need of therapeutic treatment for infection with human immunodeficiency virus is treated with an anti-HIV antiviral agent or combinations thereof. The treated individual is injected with the HIV DNA pharmaceutical compositions of the instant disclosure.

What is claimed is:

1. A synthetic polynucleotide encoding a HIV gag antigen, said polynucleotide comprising codons optimized for expression in a mammalian host as set forth in the IIIV gag open reading frame of SEQ ID NO:1.

2. The synthetic polynucleotide of claim 1, comprising the nucleotide sequence as set forth in SEQ ID NO:1.

3. The synthetic polynucleotide of claim 1, which consists of the nucleotide sequence from nucleotide 10 through nucleotide 1512 as set forth in SEQ ID NO:1.

4. A DNA plasmid vaccine vector comprising a polynucleotide sequence encoding a HIV gag antigen, said polynucleotide sequence comprising codons optimized for expression in a mammalian host, said codons as set forth in the HIV gag open reading frame of SEQ ID NO:1.

5. The DNA plasmid vaccine vector of claim 4 which comprises the polynucleotide sequence as set forth in SEQ ID NO:1.

6. The DNA plasmid vaccine vector of claim 4 which consists of the polynucleotide sequence encoding the HIV gag open reading frame from nucleotide 10 through nucleotide 1512 as set forth in SEQ ID NO:1.

7. A pharmaceutical formulation comprising the DNA plasmid vaccine vector of claim 4.

8. The DNA plasmid vaccine vector of claim 4 which comprises an operable CMV immediate-early promoter and CMV intron A 5' to the polynucleotide sequence encoding a HIV gag antigen.

9. The DNA plasmid vaccine vector of claim 4, comprising:
   a) an operable CMV immediate-early promoter and CMV intron A;
   b) a tPA signal sequence 3' to the CMV immediate-early promoter/CMV intron A; and,
   c) the polynucleotide sequence encoding a HIV gag antigen 3' to the tPA signal sequence.

10. A pharmaceutical formulation comprising the DNA plasmid vaccine vector of claim 9.

11. The DNA plasmid vaccine of claim 8 which further comprises an operable BGH termination sequence at the 3' end of the polynucleotide sequence encoding a HIV gag antigen.

12. A pharmaceutical formulation comprising the DNA plasmid vaccine vector of claim 11.

13. The DNA plasmid vaccine of claim 9 which further comprises an operable BGH termination sequence at the 3' end of the polynucleotide sequence encoding a HIV gag antigen.

14. A pharmaceutical formulation comprising the DNA plasmid vaccine vector of claim 13.

15. A method of inducing an immune response against human immunodeficiency virus in a mammalian host which comprises introducing a pharmaceutical formulation into said mammalian host, wherein said pharmaceutical formulation comprises a DNA plasmid vaccine vector comprising a polynucleotide sequence encoding a HIV gag antigen, said polynucleotide sequence further comprising codons optimized for expression in a mammalian host, said codons as set forth in the HIV gag open reading frame of SEQ ID NO:1.

16. The method of claim 15 wherein said codons are optimized codons as set forth into HIV gag open reading frame of SEQ ID NO:1.

17. The method of claim 15 wherein said DNA plasmid vaccine vector comprises an operable CMV immediate-early promoter and CMV intron A 5' to the polynucleotide sequence encoding a HIV gag antigen.

18. The method of claim 15 wherein said DNA plasmid vaccine vector comprises:
   a) an operable CMV immediate-early promoter with the CMV intron A;
   b) a tPA signal sequence 3' to the CMV immediate-early promoter and CMV intron A; and,
   c) the polynucleotide sequence encoding a HIV gag antigen 3' to the tPA signal sequence.

19. The method of claim 17 wherein the DNA plasmid vaccine further comprises an operable BGH termination sequence at the 3' end of the polynucleotide sequence encoding a HIV gag antigen.

20. The method of claim 18 wherein the DNA plasmid vaccine further comprises an operable BGH termination sequence at the 3' end of the polynucleotide sequence encoding a HIV gag antigen.

* * * * *